United States Patent
Terao et al.

(10) Patent No.: US 6,197,291 B1
(45) Date of Patent: Mar. 6, 2001

(54) AGENT FOR POTENTIATING THE EFFECT OF INTERLEUKIN-8

(75) Inventors: Toshihiko Terao; Naohiro Kanayama, both of Shizuoka (JP)

(73) Assignees: Kanebo Limited, Tokyo (JP); Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/043,974
(22) PCT Filed: Jun. 27, 1996
(86) PCT No.: PCT/JP96/01774
  § 371 Date: Oct. 14, 1998
  § 102(e) Date: Oct. 14, 1998
(51) Int. Cl.[7] ............................ A61K 38/19; A61K 38/20
(52) U.S. Cl. .................. 424/85.2; 514/2; 514/8; 514/12; 514/885; 514/169
(58) Field of Search .................. 424/85.1, 85.2; 514/2, 8, 12, 885, 169

(56) References Cited

FOREIGN PATENT DOCUMENTS

| 3209328 | 9/1991 | (JP) . |
| 6299328 | 5/1997 | (JP) . |

*Primary Examiner*—Prema Mertz
(74) *Attorney, Agent, or Firm*—Hogan & Hartson, LLP.

(57) ABSTRACT

The inventors provide an agent for potentiating the effect of interleukin-8, which comprises dehydroepiandrosterone sulfate or a pharmaceutically acceptable salt thereof as an active ingredient. An agent for potentiating the effect of IL-8 of the present invention potentiates the effect of IL-8 by activating the receptor of IL-8 and increasing the number of receptors.

4 Claims, 3 Drawing Sheets

AGENT FOR POTENTIATING THE EFFECT OF INTERLEUKIN-8

CROSS-REFERENCE TO RELATED APPLICATION

This application claims priority based on PCT Application No. PCT/JP96/01774 filed Jun. 27, 1996 identifying the United States as an elected country.

TECHNICAL FIELD

This invention relates to an agent for potentiating the effect of interleukin-8. In detail, the invention relates to an agent, which comprises dehydroepiandrosterone sulfate or a pharmaceutically acceptable salt thereof as an active ingredient, for potentiating the effect of interleukin-8.

BACKGROUND ART

Interleukin-8 (hereinafter referred to as IL-8) is a cytokine induced by monocytes, macrophages, fibroblasts, vascular endothelial cells, skin keratinized cells, renal mesangial cells, epithelial cells of intestine and respiratory tract, liver parenchyma cells and various tumor cells, and is known as a potent chemotactic factor affecting neutrophil, T-lymphocyte and basophil.

IL-8 has been reported to effectively influence the maturity of the uterine cervix in delivery and interrupted pregnancy (see WO93/09796), to have a therapeutic effect on allergic disease causing asthma, etc. by inhibiting histamine—releasing factor (HRF) from basophils (see WO92/01465), to have a therapeutic effect on Alzheimer disease and Huntington disease etc. by protective effects on the neuronal cell (see Chemical Abstracts Vol.119: 109015k), to be effective as an accelerating agent for healing wounds such as skin burns by accelerating the increase in vascular endothelial cell (see Chemical Abstracts Vol.119: 201760k) and so on. Furthermore, IL-8 is expected to develop an agent to target improvement of immunodeficiency, prevent opportunistic infection, promote anti-tumor effect, etc. by activating neutrophils and enhancing anti-bacterial effects [Zoketsu Inshi (Hematopoietic Factor), Vol.2, No.1, 46, 1991 and Med. Immunol., Vol.20, No.3, 305, 1990].

Dehydroepiandrosterone sulfate (hereinafter referred to as DHAS) or a pharmaceutically acceptable salt thereof improve the maturity of the uterine cervix and the sensitivity of uterine musculature to oxytocin in the late phase of pregnancy (see U.S. Pat. No. 4,005,200). The sodium salt performed well as an agent to improve the maturity of the uterine cervix. It is also well known that DHAS or a pharmaceutically acceptable salt thereof are effective as therapy for dementia (see U.S. Pat. No. 4,868,161), therapy and prevention of hyperlipemia (see GB2208473), therapy for osteoporosis (see U.S. Pat. No. 5,116,828) and therapy for ulcer (see Chemical Abstracts Vol. 122 142528q).

Furthermore, DHAS or a pharmaceutically acceptable salt thereof have been reported to increase the production of interleukin-2 and interleukin-4 (see WO91/04030), normalize the level of interleukin-6 induced abnormally by injury, aging and autoimmune disease (see WO93/21771).

However, neither DHAS or a pharmaceutically acceptable salt thereof has been reported to increase the effect of IL-8.

DISCLOSURE OF THE INVENTION

The inventors have now completed an invention by which DHAS or a pharmaceutically acceptable salt thereof increase the effect of IL-8 by activating both receptor, type I and type II of IL-8 receptor, and further by increasing the number of receptors.

BEST MODE FOR PRACTICING THE INVENTION

Figure 1:
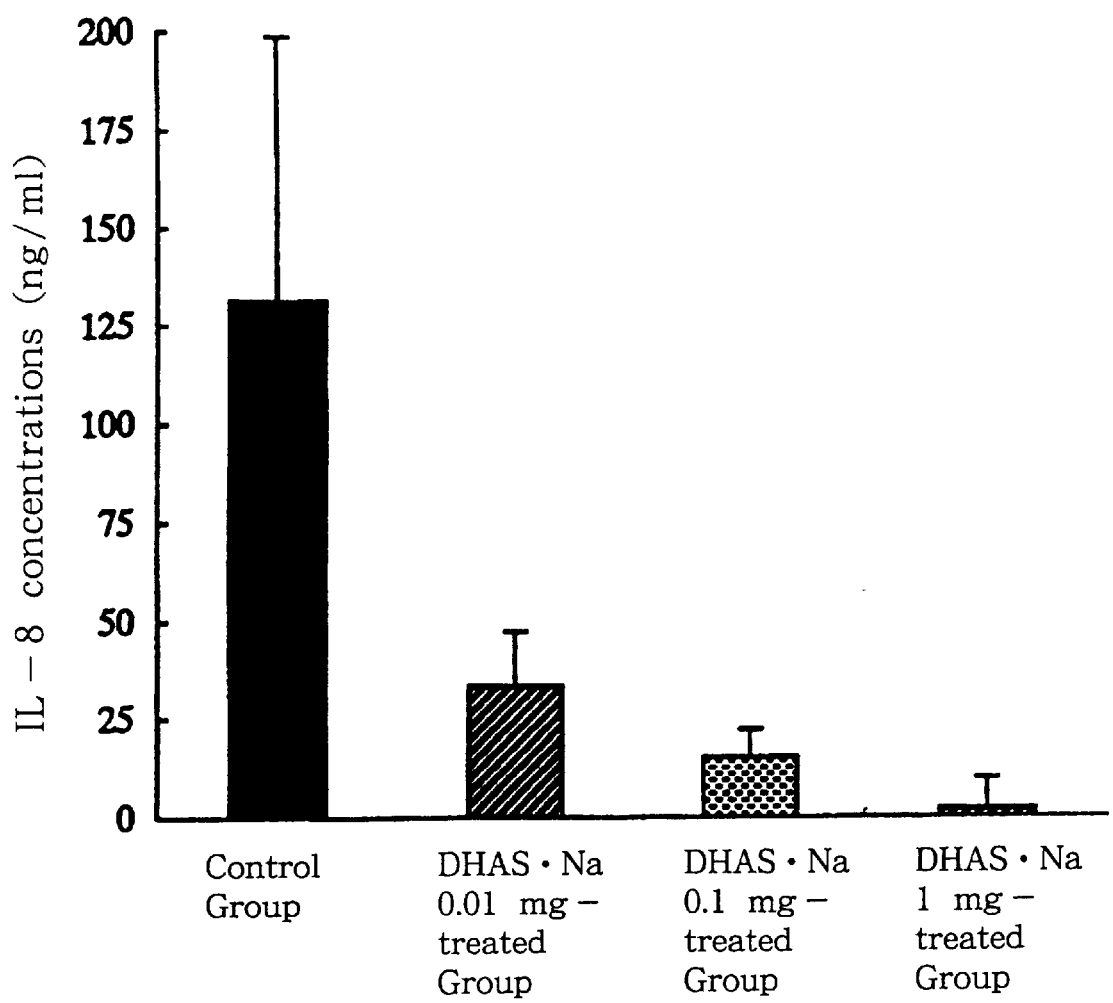
FIG. 1 is a graph showing concentrations of IL-8 in the culture supernatant of DHAS sodium salt•dihydrate (hereinafter referred to as DHAS•Na)-treated group [0.01 mg, 0.1 mg, 1 mg as DHAS sodium salt (anhydride)] and the control group.

A pharmaceutically acceptable salt of DHAS used in present invention can be for example a salt or the anhydride of alkaline metals such as sodium, potassium, etc., or a salt of organic amine such as arginine, ethanol amine, etc..

In IL-8 therapy for various diseases, for example therapy to promote the maturity of the uterine cervix in the late phase of the pregnancy, and to treat senile dementia, Alzheimer disease, Parkinson disease, Huntington disease, diabetic neuropathy, immunodeficiency, opportunistic infection, skin burn, wound, angiopathy, etc. the agent, which comprises DHAS or its pharmaceutically acceptable salts as an active ingredient, for potentiating the effect of IL-8 in present invention accelerates the therapeutic effect of IL-8 on the above diseases in combination with IL-8.

The agent for potentiating the effect of IL-8 in present invention is usually used for oral or parenteral administration to humans.

As the dosage form for oral administration, tablets, granules, fine granules, powders, etc. are mentioned. These dosage forms can be prepared by the conventional procedure by adequately mixing DHAS or a pharmaceutically acceptable salt thereof and conventional phramaceutical additives such as lactose, corn starch, crystalcellulose, magnesium stearate, hydroxypropylcellulose, talc, etc.

As the dosage form for parenteral administration, intravenous injections and suppositories are mentioned. Intravenous injections are, for example, the lyophilized form to be extemporaneously dissolved, prepared by adequately dissolving DHAS or a pharmaceutically acceptable salt thereof and stabilizers (e.g. neutral or basic amino acids, etc. such as glycine, alanine, leucine, arginine, histidine, etc. ) in purified water and freeze-drying in a conventional procedure. Suppositories are prepared, for example, by casting into molds and then cooling the melted suppository base and DHAS or a pharmaceutically acceptable salt thereof, stabilizers and absorption enhancers (e.g. neutral or basic amino acids, such as glycine, alanine, leucine, arginine, histidine, etc., or hydroxycarboxylic acid such as citric acid, L-tartaric acid), for example after they were dispersed in hard fats having a hydroxy value of not more than 50, and so on.

IL-8 in combination with an agent for potentiating the effect of IL-8 in present invention was usually administered parenterally to humans.

As the dosage form for parenteral administration of IL-8, intravenous injections, suppositories and ointments are mentioned. Intravenous injections are prepared in a conventional procedure by adequately mixing IL-8 with conventional pharmaceutical additives and then by dissolving in purified water or saline and so on. Suppositories are prepared, for example by casting into molds and then cooling the melted suppository base along with IL-8 and, if necessary, pharamaceutical additives for suppositories together, for example after they were dispersed in hard fats. Ointments are prepared in a conventional procedure by melting or dispersing IL-8 into the ointment base.

The dose of the agent for potentiating the effect of IL-8 in present invention may vary depending on the route of administration, the serverity of the symptom, the age of patient, the body weight, etc. but is usually administerd 0.5 to 100 mg/kg of DHAS per day in adults in a single dose or in the multiple doses divided in 2 or 3 doses with IL-8 at the same time, or immediately before or after the IL-8 administration.

The dose of IL-8 may vary depending on the route of administration, the serverity of the symptom, the age of patient, the body weight, etc. but is usually administerd 0.1 ng/kg to 10 mg/kg per day in adults in a single dose or in the multiple doses divided in 2 or 3 doses.

Furthermore, in the case of simultaneously administering an agent for potentiating the effect of IL-8 in present invention and IL-8, it is also possible to administer by preparing mixed preparations of DHAS or a pharmaceutically acceptable salt thereof and IL-8.

Potentiating the effect of IL-8 by DHAS or its pharmaceutically acceptable salts was evaluated using uterine cervical tissues. As a result, DHAS or a pharmaceutically acceptable salt thereof activated the receptor of IL-8 and also increased the number of receptors (see Experiment 1 as below). It was proven that they accelerated collagenase activity, elastase activity and gelatinase activity, consequently accelerated the degradation of collagen. Furthermore, these effects were markedly accelerated by a combination of DHAS or a pharmaceutically acceptable salt thereof and IL-8 (see Experiment 2 as below).

The effests of the agent of the present invention are illustrated by the following Experiments.

EXPERIMENT 1

1. Test sample

DHAS•Na

2. Experimental procedure

Biopsy specimen of uterine cervices obtained during cesarean section of pregnant women (n=8, 38 to 40 weeks of pregnancy) were dissected after accepting the agreement of the patient, divided into 2, and then incubated for 24 hours in minimum essential medium (MEM) under 37° C. and 5% $CO_2$. Half of the incubated biopsy specimens was further incubated in MEM dissolved drugs [DHAS•Na (anhydride) 0.01 mg, 0.1 mg, 1 mg], and prepared as samples for the measurement of IL-8 concentrations (hereinafter referred to as DHAS•Na-treated group). The other half of the biopsy specimen was further prepared as controls (hereinafter referred to as control group) by continuing incubation for 24 hours. IL-8 concentrations in the culture supernatant of DHAS•Na-treated and control groups were measured using a radio-immuno assay method.

Each frozen preparation from 5 random fields of the tissue of biopsy specimen in DHAS•Na-treated and control groups were stained immunohistologically for IL-8 receptor type I and type II using a Streptavidin—biotin complex—peroxidase kit (Dako, USA). Anti-IL-8 receptor type I and type II antibody was prepared using rabbits according to a method of Morohashi et al. (Journal of Leukocyte Biology, 57, 180–187, 1995). Analysis was performed by measuring the optical density and the mean was calculated. Using an image-analyzer, histological analysis was performed using a microscope connected to a video-camera.

Furthermore, the cervical tissues of DHAS•Na-treated and control groups were incubated in the medium containing IL-8-FITC complex 100 μl for 2 hours in a dark room, and then frozen preparations were prepared for observation under the fluorescence microscope.

3. Results

The results are shown in FIG. 1.

FIG. 1 is the results of IL-8 concentrations of the culture supernatant in the cervical tissues. As clearly shown in FIG. 1, IL-8 concentrations of the culture supernatant in DHAS•Na-treated group were significantly decreased compared to those in the control group. IL-8 concentrations decreased in proportion to the increase in DHAS•Na concentrations.

IL-8 receptor type I and type II incubated with DHAS•Na was more strongly stained than that in the control group. The fluorescence in DHAS•Na-treated group incubated with IL-8-FITC was markedly higher than that in the control group, and increased in a dose-dependent manner.

Taken together, DHAS or its pharmaceutically acceptable salts activate IL-8 receptor and increase the number of receptors, consequently increase binding to IL-8 receptor and decreasing IL-8 concentrations in the culture supernatant.

EXPERIMENT 2

1. Test samples (according to Preparations 1 to 4 as follows, samples for tests were prepared)

a) the virginal suppositories containing of DHAS•Na (anhydride) 10 mg (DHAS•Na-treated group)

b) the virginal suppositories containing of human recombinant IL-8 100 ng (IL-8-treated group)

c) the virginal suppositories containing of DHAS•Na (anhydride) 10 mg and human recombinant IL-8 100 ng (DHAS•Na+IL-8-treated group)

d) the virginal suppositories of placebo (control group)

2. Experimental procedure

Sixteen primigravida rabbits (day 23 of pregnancy) were divided into 4 groups, and each group of 4 rabbits was administered the test sample in the vagina once daily for 4 days. The cervices were dissected 24 hours after the administration of last suppository. Cervices were examined for consistency and dilation using Hegar's dilators. Histological sections were prepared to study the collagen content and neutrophil invasion of the cervical tissue. The collagen concentration was assessed by staining with picrosirius red (Sirius red F3BA Chroma-Gesell Schaft Schmid GmbH Co.) and validated as a histological method of determining the polymerized collagen concentration in the cervical tissues. Histological analysis was performed by measuring the optical density from 5 random fields of the tissue of each biopsy specimen and the mean optical density was calculated. In picrosirus red staining, the greater the collagen concentration, the greater the birefringence, and hence the greater the percentage of light transmission.

Histological sections were stained immunohistologically for surface antigen RT2 that is found in rabbit neutophils using anti-rabbit RT2 monoclonal antibody (Collagenase type I activity measurement, Yagai Co., Japan). The number of neutrophils (magnification×20, but avoiding cells that were within blood vessels) in 5 random fields of the tissue of each biopsy specimen was counted, and the mean was calculated From each rabbit cervix 100 mg of tissue was cut, homogenized with phosphate buffered saline, and the supernatant fluid was collected. Collagenase activity in the supernatant was measured using a specific chromogenic substrate for granulocyte elastase S-2484 (L-pyroglutamyl-L-prolyl-L-valine-p-nitroanilide, KABI Diagnostic, Sweden). Gelatinase activity was measured using a special kit (Gelatinase activity measurement, Yagai Co. Japan).

3. Results

Figure 2:
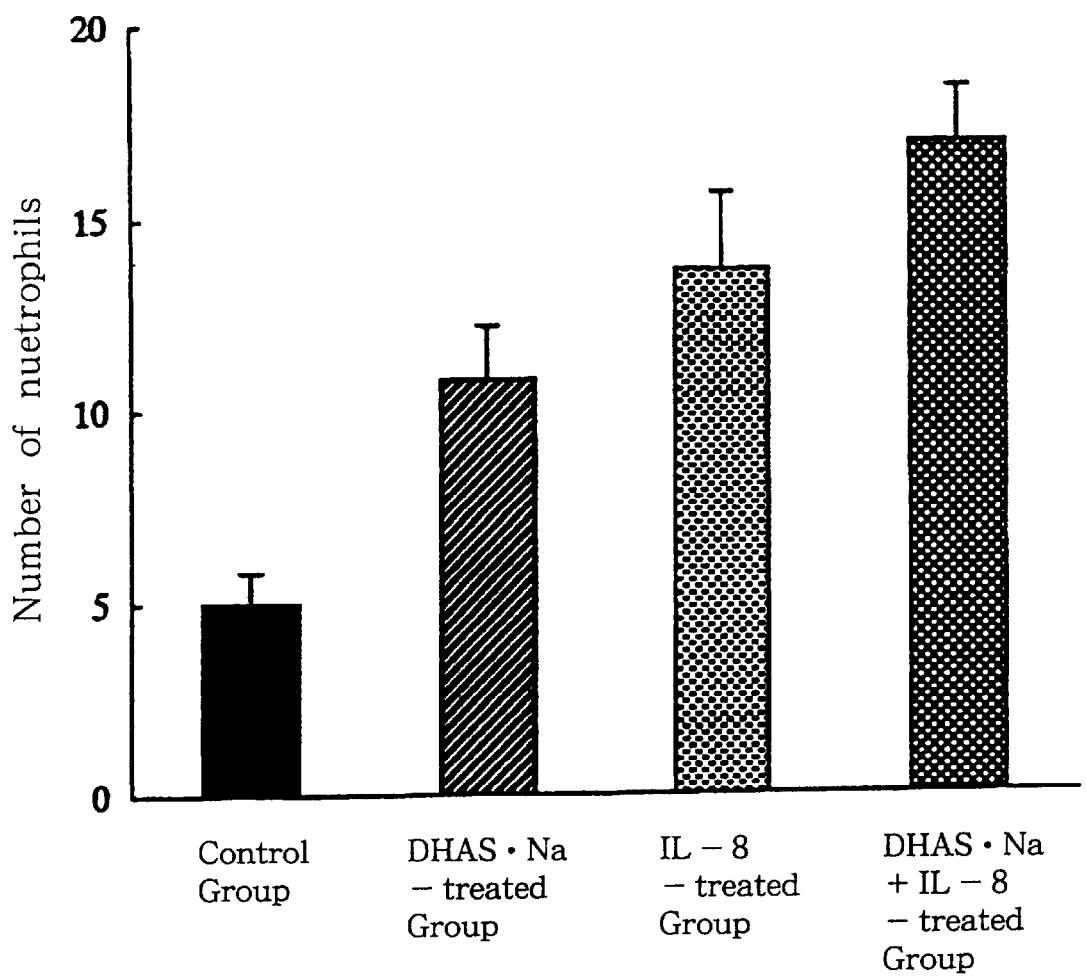
FIG. 2 is a graph showing the number of neutrophils in the uterine cervix in DHAS•Na-treated, IL-8 -treated, DHAS•Na and IL-8-treated and control groups.
Figure 3:
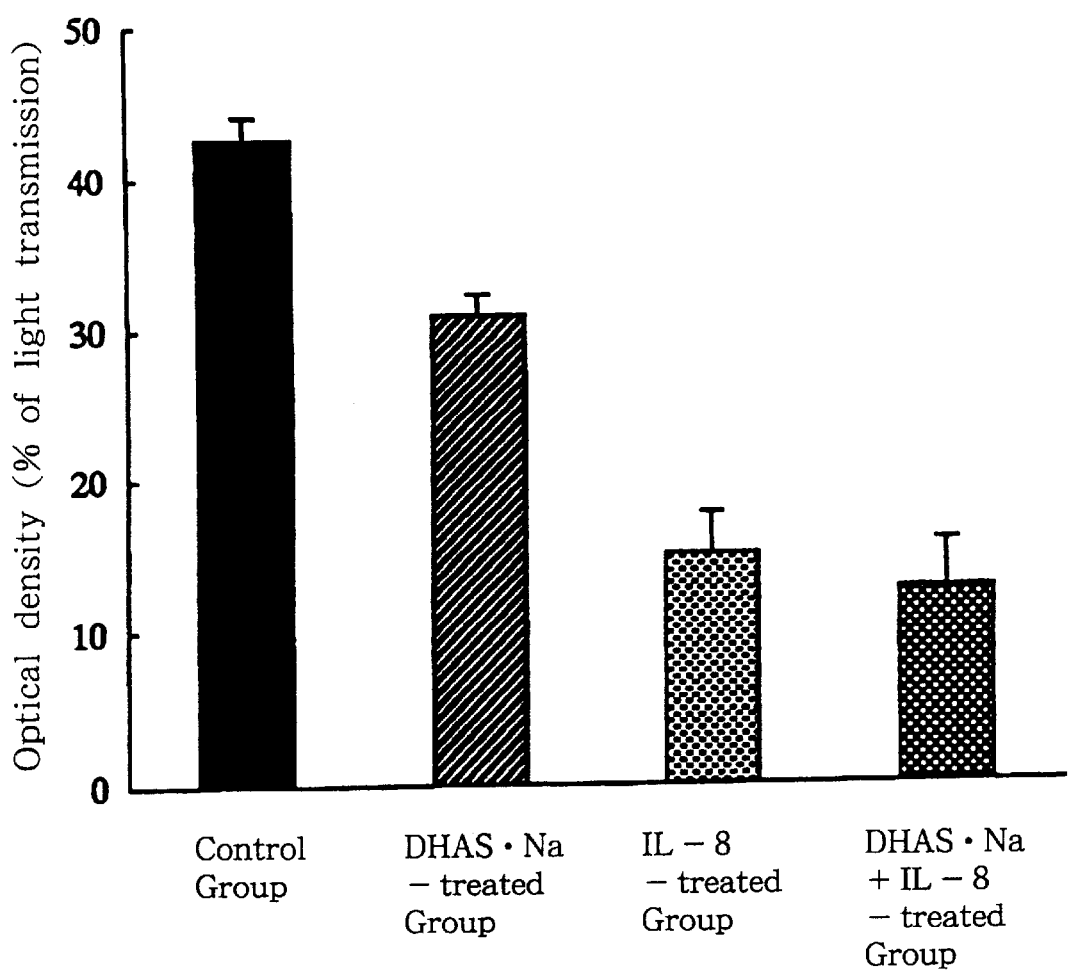
FIG. 3 is a graph showing concentrations of collagen, which were demonstrated as the optical density, in the uterine cervix in DHAS•Na—, IL-8- and DHAS•Na and IL-8-treated groups.

The results are shown in FIG. 2, FIG. 3 and Table 1.

FIG. 2 shows the number of neutrophils. Table 1 summarizes enzyme activities in each treated group. FIG. 3 shows the collagen concentrations.

TABLE 1

| Groups/<br>Enzyme | Enzyme activity (mean ± SD, U/100 mg) | | | |
|---|---|---|---|---|
| | Control | DHAS · Na | IL – 8 | DHAS · Na<br>+ IL – 8 |
| Collagenase | 0.55 ± 0.13 | 0.82 ± 0.22 | 0.92 ± 0.18 | 1.50 ± 0.18 |
| Elastase | 5.75 ± 0.96 | 9.60 ± 0.28 | 12.0 ± 1.1 | 14.9 ± 1.3 |
| Gelatinase | 7.0 ± 0.8 | 14.0 ± 0.8 | 17.0 ± 0.8 | 20.3 ± 1.3 |

As clearly shown in FIG. 2, neutrophils were significantly increased in the DHAS•Na-treated group compared to those in the control group. The number of neutrophils in the DHAS•Na+IL-8-treated group was further increased.

As clearly shown in Table 1, in collagenolytic enzymes (collagenase, elastase and gelatinase), DHAS•Na-treated group showed increased enzyme activities. DHAS•Na+IL-8-treated group showed further increases in enzyme activities.

As clearly shown in FIG. 3, the DHAS•Na-treated group showed decreased the collagen concentration, DHAS•Na+IL-8-treated group showed further decreases in the collagen concentration. Also, cervices in the DHAS•Na+IL-8-treated group were markedly soft and dilatable compared to those in the control group.

Taken together, the potentiating effect of IL-8 by DHAS or its pharmaceutically acceptable salts was evaluated using cervical tissue. Consequently, agents for potentiating the effect of IL-8 in this invention potentiated the production of neutrophils which induced the release of collagenolytic enzymes (collagenase, elastase and gelatinase) and decreased the collagen concentration, as described above by activating IL-8 receptor, increasing the number of receptors and then accelerating the binding of IL-8 to IL-8 receptor. As a result, the agents have been proved to accelerate the maturity of the uterine cervix containing collagen fiber. The effect was markedly accelerated by a combination of DHAS or its pharmaceutically acceptable salts and IL-8.

The present invention is illustrated in more detail by the following Examples and Preparations.

EXAMPLE 1

Production of tablets

[Formulation]

| Ingredient | Amount (g) |
|---|---|
| Sodium salt of DHAS · dihydrates | 109.2 |
| Lactose | 64.8 |
| Corn starch | 31.6 |

-continued

| Ingredient | Amount (g) |
|---|---|
| Hydroxypropylcellulose | 1.8 |
| Magnesium stearete | 0.6 |

[Procedure]

Sodium salt of DHAS•dihydrates, lactose and corn starch were homogeneously mixed up and the mixture was passed through a 60 mesh sieve. An aqueous solution of hydroxypropylcellulose was added to the sieved mixture, followed by kneading, and drying. Then, magnesium stearate was added and the whole mixture was tableted to give tablets each weighing 208 mg. Thus, tablets each containing 100 mg of Sodium salt of DHAS (on the anhydrate basis) are prepared.

EXAMPLE 2

Production of an injection

[Formulation]

| Ingredient | Amount (g) |
|---|---|
| Sodium salt of DHAS · dihydrates | 43.7 |
| Glycine | 40.0 |

[Procedure]

Purified water was added to glycine for dissolution of the latter. Thereto was added sodium salt of DHAS•dihydrates with warming to cause dissolution of the same. Then, the whole amount was made 2000 ml. The resultant solution was sterilized by filtration and then distributed in 5 ml portions into receptacles for injection (vials), followed by lyophilization. Thus was prepared injectable preparation to be extemporaneously dissolved, each vial containing 100 mg of DHAS•Na (on the anhydrous basis).

EXAMPLE 3

Production of virginal suppositories

[Formulation]

| Ingredient | Amount (g) |
|---|---|
| Sodium salt of DHAS · dihydrates | 43.7 |
| Glycine | 40.0 |
| Hard fat | 266.3 |

[Procedure]

Hard fat (Witepsol™ H-15, product of Huls AG) was placed in a stainless steel beaker and melted by warming at 40 to 55° C. Thereto were added sodium salt of DHAS•dihydrates and glycine, and the mixture was stirred until it became homogeneous. This mixture, while maintained at 37 to 55° C., was casted in 1.6 g poritions into spindle-shaped molds and then cooled to give vaginal suppositories each containing 200 mg of DHAS (on the anhydrous basis).

EXAMPLE 4

Production of virginal suppositories

[Formulation]

| Ingredient | Amount (g) |
| --- | --- |
| Sodium salt of DHAS · dihydrates | 43.7 |
| human recombinant IL - 8 | 0.0004 |
| Glycine | 10.0 |
| Hard fat | 266.3 |

[Procedure]

Hard fat (Witepsol™ H-15, product of Huls AG) was placed in a stainless steel beaker and melted by warming at 40 to 55° C. Thereto were added sodium salt of DHAS•dihydrates, human recombinant IL-8 and glycine, and the mixture was stirred until it became homogeneous. This mixture, while maintained at 37 to 55° C., was casted in 1.6 g poritions into spindle-shaped molds and then cooled to give virginal suppositories each containing 200 mg of DHAS (on the anhydrous basis) and 2 μg of human recombinant IL-8.

Preparation 1 [Production of virginal suppositories containing 10 mg of DHAS (anhydrate) for adminstrating animals]

[Formulation]

| Ingredient | Amount |
| --- | --- |
| Sodium salt of DHAS (on the anhydrous basis) | 100 mg |
| Glycine | 100 mg |
| Hard fat | 2 ml |

[Procedure]

Hard fat (Witepsol™ H-15, product of Huls AG) was placed in a stainless steel beaker and melted by warming at 50° C. Thereto were added sodium salt of DHAS (on the anhydrous basis) and glycine, and the mixture was stirred until it became homogeneous. This mixture, while maintained at 37 to 50° C., was casted in 0.2 ml poritions into molds and then cooled to give virginal suppositories each containing 10 mg of DHAS (on the anhydrous basis).

Preparation 2 [Production of virginal suppositories containing 100 ng of human recombinant IL-8 for adminstrating animals]

[Formulation]

| Ingredient | Amount |
| --- | --- |
| human recombinant IL - 8 | 1 μg |
| Hard fat | 2 ml |

[Procedure]

Hard fat (Witepsol™ H-15, product of Huls AG) was placed in a stainless steel beaker and melted by warming at 50° C. Thereto were added human recombinant IL-8, and the mixture was stirred until it became homogeneous. This mixture, while maintained at 37 to 50° C., was casted in 0.2 ml poritions into molds and then cooled to give virginal suppositories each containing 100 ng of human recombinant IL-8.

Preparation 3 [Production of virginal suppositories containing 10 mg of DHAS (anhydrate) and 100 ng of human recombinant IL-8 for adminstrating animals]

[Formulation]

| Ingredient | Amount |
| --- | --- |
| Sodium salt of DHAS (on the anhydrous basis) | 100 mg |
| human recombinant IL - 8 | 1 μg |
| Glycine | 100 mg |
| Hard fat | 2 ml |

[Procedure]

Hard fat (Witepsol™ H-15, product of Huls AG) was placed in a stainless steel beaker and melted by warming at 50° C. Thereto were added sodium salt of DHAS (on the anhydrous basis), human recombinant IL-8 and glycine, and the mixture was stirred until it became homogeneous. This mixture, while maintained at 37 to 50° C., was casted in 0.2 ml poritions into molds and then cooled to give virginal suppositories each containing 10 mg of DHAS (on the anhydrous basis) and 100 ng of human recombinant IL-8.

Preparation 4 [Production of placebo virginal suppositories for adminstrating animals]

[Formulation]

| Ingredient | Amount |
| --- | --- |
| Hard fat | 2 ml |

[Procedure]

Hard fat (Witepsol™ H-15, product of Huls AG) was placed in a stainless steel beaker and melted by warming at 50° C. This one, while maintained at 37 to 50° C., was casted in 0.2 ml poritions into molds and then cooled to give placebo virginal suppositories.

What is claimed is:

1. A method of therapy using IL-8 to promote maturity of the uterine cervix in late phase pregnancy, comprising the steps of:

(a) administering an amount of IL-8 to a subject in need of said therapy; and (b) administering to the subject dehydroepiandrosterone sulfate (DHAS) or a pharmaceutically acceptable salt thereof in an amount that potentiates the therapeutic effect of IL-8, thereby promoting maturity of the uterine cervix in late phase pregnancy in the subject.

2. The method of claim 1, wherein said IL-8 therapy increases activity of collagenolytic enzymes.

3. The method of claim 2, wherein said collagenolytic enzymes are collagenase, elastase or gelatinase.

4. The method of claim 1, wherein the subject is human.

* * * * *

UNITED STATES PATENT AND TRADEMARK OFFICE
CERTIFICATE OF CORRECTION

PATENT NO. : 6,197,291 B1
DATED : March 6, 2001
INVENTOR(S) : Toshihiko Terao; Naohiro Kanayama It is certified that error appears in the above-identified patent and that said Letters Patent is hereby corrected as shown below:

Title page;
Item 73, remove -- "Kanebo Limited, Tokyo (JP)" --

Signed and Sealed this

Second Day of October, 2001

Attest:

*Nicholas P. Godici*

NICHOLAS P. GODICI
*Attesting Officer*     *Acting Director of the United States Patent and Trademark Office*